United States Patent [19]

Cherksey

[11] Patent Number: 5,234,947

[45] Date of Patent: Aug. 10, 1993

[54] POTASSIUM CHANNEL ACTIVATING COMPOUNDS AND METHODS OF USE THEREOF

[75] Inventor: Bruce Cherksey, Hoboken, N.J.

[73] Assignee: New York University, New York, N.Y.

[21] Appl. No.: 790,387

[22] Filed: Nov. 7, 1991

[51] Int. Cl.$^5$ .......................................... A61K 31/335
[52] U.S. Cl. .................... 514/449; 514/450; 514/460; 514/473; 514/474; 514/812; 514/813
[58] Field of Search ............. 514/449, 450, 460, 473, 514/474, 449, 450, 460, 473, 474, 812, 813

[56] References Cited

U.S. PATENT DOCUMENTS 4,039,571  8/1977  Dawson et al. ............... 260/468

FOREIGN PATENT DOCUMENTS 63-275514   6/1988   Japan .
8902739    4/1989   PCT Int'l Appl. .
8902740    4/1989   PCT Int'l Appl. .
8912104   12/1989   PCT Int'l Appl. .

OTHER PUBLICATIONS

Kretzschmar et al., Arch Int. Pharmacodyn 180(2): 475–491 (1969).

Duty et al., "Potassium Channel Openers, Pharmacological Effects and Future Uses", *Drugs*, 40: pp. 785–791, 1990.

Edwards et al., "Structure–activity relationships of K+ channel openers", *TiPS*, vol. 11, pp. 417–422, Oct. 1990.

Edwards et al., "Potassium Channel Openers and Vascular Smooth Muscle Relaxation", *Pharmac. Ther.*, vol. 48, pp. 237–258, 1990.

Haeusler, Guenther, "K+-Channel Openers: New Antihypertensive Drugs?" *Clin. Physiol. Biochem.*, 8: (suppl. 2) pp. 45–56, 1990.

Saeed et al., "Inhibitor(s) of prostaglandin biosynthesis in extracts of oat (Avena sativa) seeds", *Biochemical Society Transaction*, 9(5): p. 444, 1981.

Tschesche et al., "Uber Triterpene-XXIX Zur Struktur Des Avenacins", *Tetrahedron*, vol. 29, pp. 629–663, 1973.

Output generated from Compact Cambridge: MEDLINE 1988 Revised for 1990, search Strategy: AVENCAB: Document 3 of 5.

C. L. Anand, "Effect of Avena sativa on Cigarette Smoking", *Nature*, vol. 233, p. 496, Oct. 15, 1971.

Mrs. M. Grieve, "The Medicinal, Culinary, Cosmetic and Economic Properties, Cultivation and Folk-Lore of Herbs, Grasses, Fungi Shrubs & Trees, with all their Moders Scientific Uses", *J. Pharm. Pharmac.*, 27: 92–98, 1975.

*Primary Examiner*—S. J. Friedman
*Assistant Examiner*—William Jarvis
*Attorney, Agent, or Firm*—Pennie & Edmonds

[57] ABSTRACT

A method for activating potassium channels and for treating hypertension, addiction, asthma, incontinence, and other conditions treatable by potassium channel activators, such as spasms and convulsions, comprising administering a compound having the formula:

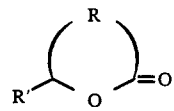

wherein R is a saturated or unsaturated group having from 1 to 4 carbon atoms which is optionally substituted by lower alkyl, lower alkenyl or lower alkoxy groups; and wherein R' is hydrogen, lower alkyl, lower alkenyl, or aralkyl.

5 Claims, 1 Drawing Sheet

POTASSIUM CHANNEL ACTIVATING COMPOUNDS AND METHODS OF USE THEREOF

FIELD OF THE INVENTION

The present invention relates to compounds and compositions which have been found useful in potassium channel activation, treatment of hypertension, alleviation of the symptoms of addition withdrawal, and all other conditions treatable by a potassium channel opener, and to methods of use of these compounds.

BACKGROUND OF THE INVENTION

*Avena sativa*, or common oats, is an annual grain which is widely cultivated for its edible grain, sometimes called groats. Beneficial properties have long been attributed to oats, as evidenced by such common expressions as "feeling your oats." Persons who ascribe to "natural medicine" or "herbal science" have included oats in their armamatum of purportedly therapeutic preparations. Indeed, over the years scattered reports of pharmacological activity attributable to some component in oats have appeared in the traditional scientific literature, most recently with respect to the cholesterol-lowering properties of oat bran.

There have been reports in the popular literature of the use of alcoholic extracts of *Avena sativa* as treatments for both opiate addiction and cigarette smoking. However, the scientific literature has not documented any anti-addictive activity of any of the chemically defined compounds in *Avena sativa*.

Handler, in *The Doctors' Vitamin and Mineral Encyclopedia*, Simon and Schuster, New York, 1990, 318–319, notes that there have been claims that oats have anti-depressant and aphrodisiac properties, and there is some evidence that oats can aid people in overcoming drug habits. A decoction of common oats has been successfully used in Ayurvedic medicine to treat opium addiction. It was noted along the way that several opium addicts, in addition to curbing opium withdrawal, also lost interest in smoking cigarettes after using an alcoholic extract of the oat plant. Anand, in *Nature*, 233: 496, 1971, described an experiment in which chronic cigarette smokers were given an extract of fresh *Avena sativa*. This study was placebo controlled, and found that, after one month, there was a significant decrease in the number of cigarettes smoked by those using oat extract when compared to those using a placebo. A diminished craving was definitely noted, and the effect continued two months after the oat extract treatments had ceased. A subsequent study on mice suggested that the oat extract contains substance that is antagonistic to morphine. The claimed anti-depressant and aphrodisiac properties of oats have never been convincingly demonstrated.

According to Lust, in *The Herb Book*, Bantam Books, New York, 1974, 286–287, oats are used primarily for their nutritional value. They are particularly beneficial in special diets for convalescents or those with certain illnesses, including gastro-enteritis and dyspepsia. Oat extract and tincture are useful as nerve and uterine tonics. A tea made from oat straw has been recommended for chest problems.

Saeed et al., in *Biochemical Society Transactions*, 9(5):444 (1981), reported on an evaluation of extracts of oats in inhibiting prostaglandin biosynthesis. Extracts of *Avena sativa* were found to possess strong inhibitory activity of prostaglandin biosynthesis, which may explain the anti-inflammatory effects of oats on certain inflammatory conditions of the skin, including itch, sunburn, and like conditions.

Tschesche et al., in *Tetrahedron*, 29: 629–633, 1973, report the extraction of an antibiotic active glycoside, avenacine B, from the roots of *Avena sativa*. This glycoside was isolated in addition to the main glycoside, avenacine A. The aglycone B substitutes a methyl group for the hydroxymethyl group of the aglycone A.

Erickson, in *Photochem. Photobiol.* 49(4): 479–483, 1989, disclose the visualization of a highly purified photochrome from *Avena sativa* by electron microscopy after negative staining with uranyl acetate and after rotary shadowing with platinum. The particle shape was variable in both types of specimens, but tripartite structures resembling a "Y" were consistently observed. The tripartite substructure is composed of three globular domains, each having a diameter of 7 to 8 nm and equally spaced in an equilateral triangle. The dimensions of the tripartite particle measured 15 nm between the centers of any two of the three particles. When the phytochrome was digested with trypsin to release the amino-terminal globular domain from the polypeptide, the tripartite structure was lost. It was proposed that the outer particles of the tripartite structure are the amino-terminal domains of the phytochrome dimer, and the central particle comprises the carboxyl domains of the two subunits.

The tetrahydropyranone structure is a major feature of a series of aromatic compounds obtained from piper methysticin Forst, the Polynesian kava—kava plant, also known as intoxicating pepper. A number of aromatic pyrones have been identified in kava—kava extracts; all of these compounds are unsaturated across the 3,4-positions and contain a methoxy group in the 4-position:

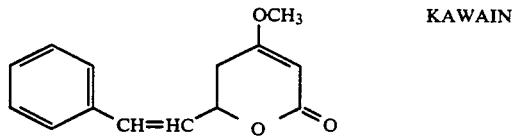

KAWAIN

The compounds identified in the kava kava include kawain, dihydrokawain, methysticin, dihydromethysticin, yangonin and desmethoxyyangonin. These compounds are well known in the popular literature, and have been studied for a number of pharmacological activities.

Kava kava has a long history of use in the Polynesian islands, particularly Fiji. Traditionally, the upper rhizome is made into a tea. The tea was considered to act as a mild stimulant and tonic. Another method of treating the plant involved first chewing on the root, spitting it into a bowl, and then soaking it in coconut milk. This preparation reportedly possesses narcotic-like properties.

The primary effects of kava kava extract are initially, and at low dose, euphoric. Larger doses produce extreme relaxation, lethargy of the lower limbs, and finally, sleep. Frequently, larger doses of kava kava may produce visual and auditory hallucinations. Chewing the kava kava root produces a numbing of the mouth.

A number of studies have appeared in the scientific literature, and are referenced in the Merck Index.

Kretzschmar et al., in *Arch. Int. Pharmacodyn* 177: 261–277, 1969, report an investigation into the anticonvulsant activities of the kava compounds. All six kava-pyrones were used to antagonize convulsions in mice caused by maximal electroshock and phenyltetrazol. The results were compared to standard anti-convulsants, including dilantin and phenobarbital. All six kava compounds were found to be active as anti-convulsants. However, the effects were more similar to the effects of local anesthetics such as procaine than to the traditional anti-convulsants. The anticonvulsant effect was antagonized by pretreatment with reserpine. No structure-activity relationships were apparent for intravenous dosage. The effective dose was between 5 and 10 mg/kg. The lethal dose was between four and ten times higher for i.v. administration, and about 1 gram/kg for oral administration. These results suggest a neurotransmitter mediated mechanism due to the antagonism by reserpine, and possibly an effect on membrane channels to account for the procaine-like effects.

In *Arch. Int. Pharmacodym* 180: 475–491, 1969, Kretzschmar et al. report studies of the spasmolytic activities of the kava-pyrones using the guinea pig isolated ileum preparation. All six of the kava compounds were found to have spasmolytic activity. Histamine, 5-HT, acetylcholine and nicotine were used to induce muscle contractions, and the ability of the kava pyrones to antagonize this activity was tested. The kava-pyrones were found to antagonize the effects of all of the stimulants. Thus, the mechanism of the kava-pyrones was not due to a specific receptor-mediated mechanism at the transmitter level but were considered to be direct musculotropic actions similar to that of papaverine. The kava-pyrones were most potent against contractions due to nicotine and 5-HT, and less active against acetylcholine and histamine. The authors again attempted to compare the results with those obtained by local anesthetics, and found the highest correlation with benzocain and cocaine and less correlation with procaine. There was a clear relationship between structure and activity for the kava pyrones: compounds which are completely saturated in the pyrone ring, i.e., the tetrahydropyrones, were more effective than compounds that were saturated in the 5,6-position, the dihydropyrones. Substitution on the benzene ring of these compounds was found to alter their activity. No compounds lacking the 4-methoxy group on the pyrone ring were tested.

Gamma and delta lactones are known to be flavor and fragrance compounds. Methods of producing such lactones are disclosed, for example, in Page et al., PCT application WO89/12104. Japanese patent 63/275514 discloses lactone compounds for use in hair tonics for inhibiting the activity of testosterone-5-reductases.

Voltage-gated potassium channels make up a large molecular family of integral membrane proteins that are fundamentally involved in the generation of bioelectric signals such as nerve impulses. These proteins span the cell membrane, forming potassium-selective pores that are rapidly switched open or closed by changes in membrane voltage. Several chemical entities have been discovered to be potent and specific openers of vascular potassium channels. These include cromakalim and its derivatives and RP 52891. This mechanism is also shared, at least partially, by drugs such as minoxidil, diazoxide, pinacidil and nicorandil. The opening of plasmalemmal K+ channels produces loss of cytosolic K+. This effect results in cellular hyperpolarization and functional vasorelaxation. In normotensive or hypertensive rats, K+ channel activators decrease aortic blood pressure (by producing a directly mediated fall in systemic vascular resistance) and reflexly increase heart rate. K+ channel openers produce selective coronary vasodilatation and afford functional and biochemical protection to the ischemic myocardium.

SUMMARY OF THE INVENTION

It is an object of the present invention to provide compounds having the property of potassium channel activation.

It is another object of the present invention to provide compounds which have hypotensive activity.

It is a further object of the present invention to provide compounds useful in alleviating the symptoms of addiction withdrawal.

It is yet another object of the present invention to provide methods for treating hypertension.

It is still another object of the present invention to provide methods for alleviating the symptoms of withdrawal from an addictive substance.

It is yet another object of the present invention to provide a method for treating any condition which may be alleviated by potassium channel activation.

It is yet a further object of the present invention to provide a method for activating potassium channels in vivo.

It has been discovered that compounds of the following formula have the property of potassium channel activation:

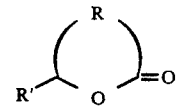

wherein R is a saturated or unsaturated moiety of one to four carbon atoms, so as to create a four- to seven-membered ring structure, which ring structure may be saturated or unsaturated, and the carbon atoms of which may be substituted by lower alkyl, lower alkenyl groups or lower alkoxy groups, and R' may be hydrogen, lower (e.g., $C_1$–$C_8$) alkyl, lower alkenyl or aralkyl in which the alkyl portion is preferably lower alkyl.

The compounds of the present invention may be used to treat withdrawal symptoms from any addictive substance, such as cigarettes, alcohol or narcotic drugs. As this utility has been discovered to be an effect of the potassium channel activation properties of these compounds, any compounds known to be a potassium channel activator can be used for the treatment of withdrawal symptoms from addictive substances. Non-limiting example of compounds having the property of potassium channel activation are RP 52891, cromakalim, lemakalim, celikalim, RO-316930, 507-PC0-400, HOE-234, minoxidil, diazoxide, pinacidil, and nicorandil.

The compounds of the present invention may also be used for the treatment of any condition which is treatable by potassium channel activators, such as hypertension, incontinence, asthma, etc.

DETAILED DESCRIPTION OF THE INVENTION

Avena pyrone, 2H-6-methyltetrahydropyran-2-one, has the following formula:

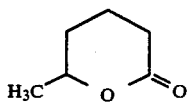

This compound can be extracted from *Avena sativa* by methods including distillation, extraction and HPLC. In order to obtain avena pyrone from oats, an alcoholic extract of oats may be evaporated under reduced pressure at 60° C. using a rotovap. The residue is brought up in water and vacuum distilled at 90°–100° C. The resulting distillate contains both anti-addiction and stimulating activities. This distillate is subjected to anion exchange HPLC which reveals two groups of substances. Fraction 2, substantially the anionic group of compounds, contains the stimulant activity. Fraction 1, the weakly anionic to non-anionic fraction, is devoid of stimulant activity but is found to contain the antiaddiction activity. Surprisingly, when the two groups of substances are separated, the neutral fraction, Fraction 1, is found markedly to lower blood pressure in a manner consistent with vasodilation/smooth muscle relaxation. This activity has never been reported for *Avena sativa*, perhaps because of the pronounced stimulant activity of previously used extracts, which might have masked the hypotensive activity.

The hypotensive agent may be further purified from the extract using organic extraction techniques. Initially, the distillate is made basic using 5% sodium carbonate and extracted with ethyl acetate. The active compound is found to reside in the mother liquor, and need not be extracted. The water phase is then acidified using concentrated hydrochloric acid and again extracted with ethyl acetate. Again, the active compound need not be extracted.

After HPLC, the mother liquor is sufficiently pure to perform structural studies. The water phase is dried by lyophilization and subjected to NMR and mass spectral analysis. The active compound proves to be a substituted tetrahydropyran, 6-methyl-tetrahydropyran-2-one.

Isolated avena pyrone was studied for its action against ionic channels in cell membranes using the lipid bilayer technique. Membranes from rat brain were fused with a lipid bilayer formed across the opening of a patch-clamp pipette. Electrical activity was monitored using an Axon Instruments Axopatch amplifier using 100 mM symmetrical KCl solutions. In the presence of elevated levels of calcium, at least three types of potassium channel can be determined: a small 25–50 pS channel, a 90–120 pS channel, and a large 200–220 pS channel. In the absence of calcium in the bathing solutions, openings of the large 200 pS channel are rarely seen. When avena pyrone is added to the bathing solution, an activation of the large K+ channel is seen, evidenced by an increased open probability and very long open times.

Figure 1:
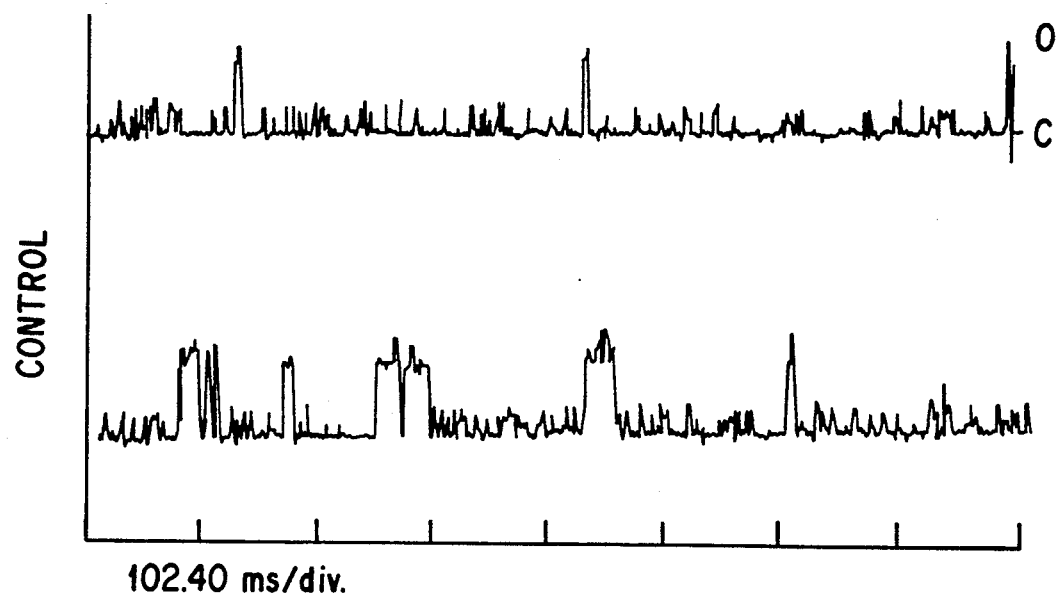
FIG. 1 shows monitoring of electrical activity of rat brain membranes in a potassium chloride solution.
Figure 2:
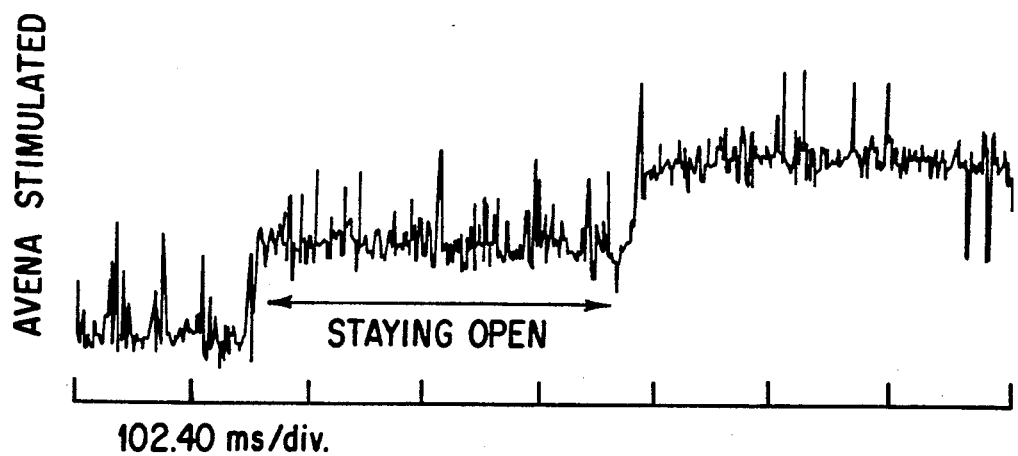
FIG. 2 shows monitoring of electrical activity of rat brain membranes in a potassium chloride solution which also includes avena pyrone.

FIGS. 1 and 2 show the exposure of the channels to potassium in the presence of avena pyrone. In the two tracings in FIG. 1, the membrane potential was held at −25 mV. Under these conditions, the mid-sized K+ channel is very active but the large channel is rarely open during the approximately 1.5 seconds shown.

When avena pyrone was added to the bath, the large channel was activated, as shown in FIG. 2. It was then apparent that there were either four or five of the large channels in the membrane, and the opening times increased from a few milliseconds to times approaching seconds. Because of this it is now possible for there to be multiple channels open at once, suggesting that the open probability for the large channel in the absence of avena pyrone is very low. The effect is most pronounced under low calcium conditions. Under conditions of greater calcium concentration, the pyrone is still capable of activation of the channel but to a lesser degree, as the channel is already active. Thus, it appears that avena pyrone operates as a K+ channel activator, substantially increasing the open probability of the large Ca++- dependent channel.

The action of avena pyrone in K+ channels is consistent with the physiological activity of smooth muscle relaxation and the other activities of *Avena sativa*. The opening of K+ channels in a cell membrane effectively electrically shunts the membrane, preventing excitation-contraction. The hypotensive vasodilators pinacidil and cromakalim work in precisely this manner.

The interference with the effects of withdrawal symptoms from addictive substances of the subject compounds is also consistent with potassium channel activation. For example, with respect to cigarette smoking, the effect of avena pyrone is to reduce the craving for a cigarette. As one gets a craving for a cigarette, there is a perception of muscular tension. The effects of potassium channel activators are to lower the blood pressure, relax the muscles and make breathing easier, all of which counteracts the feeling of craving one experiences upon withdrawal from an addictive substance.

Besides the avena pyrone, another known natural compound having the structure of the present invention is parasorbic acid (or parasorbinic acid), which is the dihydro analoq of avena pyrone and has the following structure:

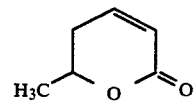

Parasorbic acid is a natural product which has been isolated from the berries of mountain ash (Rowan), or *Sorbus aucuparia L., Rosaceae*. The juice of the berries has been used as an astringent and as a mouthwash. The berries contain a high concentration of vitamin C and are also considered to to be antiscorbutic as well as a mild diuretic. In northern Europe, a strong spirit is made from Rowan berries. Parasorbic acid is the major, if not exclusive, product obtained by steam distillation of acidified berries.

The antispasmodic effect of aryl-substituted α-pyrones from the kava-root have previously been reported, although it was not known that these effects were due to the property of potassium channel activation. It has now been confirmed that kawain is indeed a potassium channel activating substance. All of the kava pyrones have a bulky aromatic group. It has unexpectedly been found that the substitution of a lower alkyl group for the more bulky aromatic group enhances the potassium channel activation effects of the compounds.

While the kava pyrones were known to have anti-convulsant and anti-spasmodic properties, it was not known that they had potassium channel activation effects, and therefore it would not have been obvious from their known anti-convulsive and anti-spasmodic effect that they could also be used for the treatment of hypertension or the treatment of addiction withdrawal symptoms, or any of the other effects of potassium channel activation which do not involve the anti-convulsant or anti-spasmodic effects of the compounds.

The dosages required of the compounds of the present invention for treating addiction and for treating hypertension can be readily determined by a physician, depending upon the individual response of each patient. Examples of effective doses for treating each of the above conditions range from about 0.5–20 mg/kg of body weight. Individual dosages can readily be determined by patient reaction to the drug.

The compounds of the present invention can be administered in the form of pharmaceutically acceptable compositions, that is, with the active ingredient mixed with or encapsulated by a pharmaceutically acceptable carrier. Compositions within the scope of the invention thus include compositions wherein the active component is present in an effective amount to achieve its intended purpose. Determination of the effective amounts is well within the skill of the art.

In addition to the compounds of the present invention, these pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.1 to 99 percent, and preferably from about 1–85 percent of active ingredient, together with a suitable excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture, and processing the mixture of granules, after adding suitable auxiliaries, if desired or necessary, to obtain tablets of dragee cores.

Examples of suitable excipients include lactose, sucrose, mannitol, sorbitol, cellulose preparations, calcium phosphates, binders such as starch paste from maize starch, wheat starch, rice starch, potato starch, gelatin, tragacanth, methyl cellulose, hydroxypropylmethylcellulose, sodium carboxymethylcellulose and/or polyvinylpyrrolidone. If desired, disintegrating agents may be added, such as the above-mentioned starches as well as carboxymethyl starch, crosslinked polyvinyl pyrrolidone, agar, alginic acid, sodium alginate, and the like.

Auxiliaries include flow-regulating agents and lubricants such as silica, talc, stearic acid or salts thereof and/or polyethylene glycol. Dragee cores are provided with suitable coatings which, if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures.

In order to produce coatings resistant to gastric juices, solutions of suitable cellulose preparations such as acetyl cellulose phthalate of hydroxypropylmethylcellulose phthalate are used. Dyestuffs or pigments may be added to the tablets or dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with filler such as lactose, binder such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example suppositories, which consist of a combination of the active compounds with a suppository base. Suitable suppository bases are, for example, natural or synthetic triglycerides, paraffin hydrocarbons, polyethylene glycols or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous suspensions of the active ingredients, as well as appropriate oily injection suspensions. Suitable lipophilic vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, and/or dextran. Optionally, the suspension may also contain stabilizers.

The compounds of the present invention may be administered in a variety of convenient forms, orally, parenterally, rectally, or percutaneously to treat addiction and/or hypertension. The period of treatment can range from several days to treat addiction to administration periodically, e.g., weekly, to treat hypertension. The dosage required for each patient may vary widely, depending upon the degree of hypertension or addiction treated and the individual patient response. However, in general, a dosage of from about 0.1 to about 10 mg/kg body weight is appropriate for most patients.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method of alleviating the symptoms of tobacco addiction withdrawal or nicotine addiction withdrawal in a subject, comprising administering to the subject an effective amount of a compound having the formula:

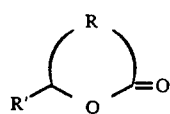

wherein R is a saturated or unsaturated group having from 1 to 4 carbon atoms which is optionally substituted by lower alkyl, lower alkenyl or lower alkoxy groups, and wherein R' is selected from the group consisting of hydrogen, lower alkyl, lower alkenyl and aralkyl.

2. The method according to claim 1 wherein the compound is selected from the group consisting of 2H-6-methyltetrahydropyran-2-one and parasorbic acid.

3. A method for treating a spastic or convulsive condition in a subject, comprising administering to the subject an effective amount of a compound having the formula:

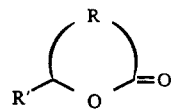

wherein R is a saturated or unsaturated group having from 1 to 4 carbon atoms which is optionally substituted by lower alkyl, lower alkenyl or lower alkoxy groups, and wherein R' is selected from the group consisting of hydrogen, lower alkyl, lower alkenyl and aralkyl.

4. A method in accordance with claim 3 wherein R' is hydrogen, lower alkyl or lower alkenyl.

5. A method for alleviating the symptoms of tobacco addiction withdrawal or nicotine addiction withdrawal in a subject, comprising administering to the subject an effective amount of a compound having the properties of potassium channel activation.

* * * * *

UNITED STATES PATENT AND TRADEMARK OFFICE
CERTIFICATE OF CORRECTION

PATENT NO. : 5,234,947

DATED : August 10, 1993

INVENTOR(S) : Bruce Cherksey

It is certified that error appears in the above-identified patent and that said Letters Patent is hereby corrected as shown below:

Column 9, line 21: Change "spastic" to –spasmodic–.

Signed and Sealed this

Twenty-ninth Day of November, 1994

Attest:

BRUCE LEHMAN

Attesting Officer   Commissioner of Patents and Trademarks